United States Patent [19]
Reifschneider et al.

[11] Patent Number: 4,588,711
[45] Date of Patent: May 13, 1986

[54] INSECTICIDAL PHOSPHORUS DERIVATIVES OF 6-CYCLOALKYL-4-PYRIMIDINOLS

[75] Inventors: Walter Reifschneider, Walnut Creek; Doris L. Paroonagian, Pleasant Hill; Mark J. Costales; Donald H. DeVries, both of Concord, all of Calif.

[73] Assignee: The Dow Chemical Company, Midland, Mich.

[21] Appl. No.: 619,513

[22] Filed: Jun. 11, 1984

Related U.S. Application Data

[63] Continuation of Ser. No. 443,420, Nov. 22, 1982, abandoned.

[51] Int. Cl.⁴ ............................ A01N 57/08; C07F 9/65
[52] U.S. Cl. .................................... 514/86; 544/243; 544/319; 544/321
[58] Field of Search ................... 544/243; 424/200; 514/86

[56] References Cited

U.S. PATENT DOCUMENTS

| | | | |
|---|---|---|---|
| 3,457,278 | 7/1969 | Zimmermann | 544/318 X |
| 3,951,975 | 4/1976 | Hofer et al. | 544/243 |
| 4,012,506 | 3/1977 | Balke et al. | 424/200 |
| 4,127,652 | 11/1978 | Maurer et al. | 424/200 |
| 4,202,889 | 5/1980 | Maurer et al. | 424/200 |
| 4,254,113 | 3/1981 | Maurer et al. | 424/200 |
| 4,261,983 | 4/1981 | Maurer et al. | 424/200 |
| 4,325,948 | 4/1982 | Maurer et al. | 424/200 |
| 4,326,059 | 4/1982 | Gargano et al. | 544/243 |
| 4,380,538 | 4/1983 | Maurer et al. | 424/200 |

*Primary Examiner*—Nicholas S. Rizzo
*Assistant Examiner*—Diana G. Rivers
*Attorney, Agent, or Firm*—S. Preston Jones; Ronald G. Brookens

[57] ABSTRACT

Disclosed are phosphorus derivatives of 6-cycloalkyl-4-pyrimidinols and their utility as insecticides which possess both systemic and foliar activity for plants against insect pests.

30 Claims, No Drawings

INSECTICIDAL PHOSPHORUS DERIVATIVES OF 6-CYCLOALKYL-4-PYRIMIDINOLS

CROSS-REFERENCE TO RELATED APPLICATION

This is a continuation of application Ser. No. 443,420, filed 11/22/82, now abandoned.

BACKGROUND OF THE INVENTION

The present invention relates to new phosphorus derivatives of 6-cycloalkyl-4-pyrimidinols which possess insecticidal properties and especially both systemic and foliar activity for plants against insect pest. The present invention is also directed to the preparation of said derivatives, active insecticidal compositions containing said derivatives and to the use of such compositions for the kill and control of said pest.

SUMMARY OF THE INVENTION

The present invention is directed to phosphorus derivaties of 6-cycloalkyl-4-pyrimidinols which correspond to the formula

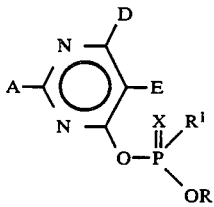

(Formula I)

wherein;

A represents hydrogen, alkyl, cycloalkyl, alkoxy, perfluoroloweralkyl, alkylthio, alkylsulfinyl, alkylsulfonyl, dialkylamino or phenyl;

D represents cyclopropyl, 1-methylcyclopropyl or cyclobutyl;

E represents hydrogen, alkyl or halo;

X represents oxygen or sulfur;

R represents alkyl; and $R^1$ represents alkyl, alkoxy, alkylthio, monoalkylamino or phenyl.

These above compounds have been found to have good pesticidal properties especially insecticidal, miticidal, acaricidal and nematicidal properties. The compounds also have systemic activity in plants and foliar activity on plants against attack by said pest.

In the present specification and claims, the terms "alkyl", and "alkoxy" as employed in the terms "alkyl", "alkoxy" or as a part of the terms "alkylthio", and "dialkylamino" designates straight or branched chain alkyl or alkoxy groups of 1 to 4 carbon atoms.

In the present specification and claims, the term "cycloalkyl" as employed in the term "cycloalkyl" or as a part of the terms "alkyl(cycloalkyl)", "(cycloalkyl)alkyl" designates a cycloalkyl group of from 3 to 4 carbon atoms.

The term "perfluoroloweralkyl" designates a perfluoroalkyl group of 1 to 3 carbon atoms.

The term "halo" designated bromo, chloro or fluoro.

The compounds of the present invention are largely somewhat viscous oils or solids which are rather readily soluble in many common organic solvents and of low solubility in water.

The compounds of the present invention can be prepared by the reaction of substantially equimolar amounts of an appropriate 4-pyrimidinol reactant corresponding to the formula

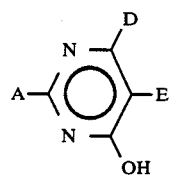

wherein A, D and E are as hereinbefore defined, and an appropriate phosphorochloridate or phosphorochloridothioate corresponding to the formula

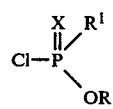

wherein R and $R^1$ are as hereinbefore defined in the presence of a solvent and a hydrogen chloride absorber.

In carrying out the reaction, the reactants are mixed in any suitable fashion and maintained together with agitation until the reaction is complete. It is convenient to first mix the pyrimidinol with the solvent and the HCl acceptor and then add the phosphorus reactant. The reaction is complete when all of the phosphorus reactant has been consumed.

Representative solvents include, for example, acetonitrile, cyclohexane, benzene, toluene, xylene, acetone, methylene chloride, methylethyl ketone, diethylether, dioxane, tetrahydrofuran and the like.

Representative hydrogen chloride absorbers (acid-binding agents) include, for example, alkali metal carbonates such as sodium and potassium carbonates and tertiary amines such as, for example, trimethylamine, triethylamine, pyridine and the like.

At the completion of the reaction, the reaction mixture is filtered to remove any insolubles and the filtrate concentrated under reduced pressure. The residue is then taken up in a solvent such as ethyl ether, benzene, toluene, methylene chloride or chloroform and then washed thoroughly with an aqueous sodium hydroxide solution and then with a saturated sodium chloride solution and dried. The solvent is removed by evaporation under reduced pressure leaving the desired product.

DESCRIPTION OF SOME PREFERRED EMBODIMENTS

The following examples illustrate the present invention and the manner by which it can be practiced but, as such, should not be construed as limitations upon the overall scope of the same.

EXAMPLE 1

O,O-Diethyl O-(6-cyclopropyl-2-methyl-4-pyrimidinyl)phosphorothioate

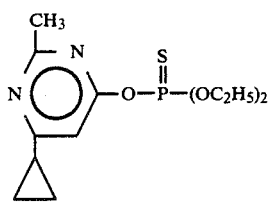

A mixture of 5.0 grams (g) of 6-cyclopropyl-2-methyl-4-pyrimidinol, 5.9 g of finely powdered potassium carbonate, 60 milliliters (ml) of acetonitrile and 6.2 g of O,O-diethyl phosphorochloridothioate was stirred and heated under reflux for two hours. At this time, no more of the starting phosphorus compound could be detected by gas-liquid chromatography (glc). The salts which formed were removed by filtration and the filtrate concentrated under reduced pressure. The residue was taken up in ether, the ether solution washed twice with 5% aqueous sodium hydroxide solution, once with saturated sodium chloride solution and dried over anhydrous sodium sulfate. The ether was removed in a rotary evaporator leaving 8.9 g (90 percent of theoretical) of the above-indicated product as a pale amber colored oil having a refractive index of n(25/d)=1.5191. The infrared (IR) and nuclear magnetic resonance (NMR) spectra were consistent with the desired structure. Upon analysis, the product was found to have carbon, hydrogen and nitrogen contents of 47.66, 6.33 and 9.19 percent, respectively, as compared with the theoretical contents of 47.67, 6.33 and 9.27 percent, respectively, as calculated for the above-named structure.

By following the preparative procedures as outlined in the above methods of preparation and the above examples and employing the appropriate starting materials, the following compounds set forth in Table 1 are prepared.

TABLE 1

| A | D | E | X | R | $R^1$ | RI (25°) M.p. °C. |
|---|---|---|---|---|-------|-------------------|
| H | ▷ | H | S | $C_2H_5$ | $OC_2H_5$ | 1.5235 |
| H | ▷ | H | S | $C_2H_5$ | $NHC_2H_5$ | 1.5415 |
| H | ▷ | Cl | O | $CH_3$ | $SCH_3$ | |
| H | ▷ | Br | S | $CH_2CH_2CH_3$ | $OCH_2CH_2CH_3$ | |
| H | ▷-CH$_3$ (gem-dimethyl) | H | O | $C_2H_5$ | $SCH_2CH_2CH_3$ | |
| H | ▷-CH$_3$ (gem-dimethyl) | $CH_3$ | O | $C_2H_5$ | $NHCH(CH_3)_2$ | |
| H | ◇ | H | S | $CH_3$ | $OCH_3$ | |
| H | ◇ | H | S | $C_2H_5$ | $NHCH_3$ | |
| —$CH_3$ | ▷ | H | S | $CH_3$ | $OCH_3$ | 1.5325 |
| —$CH_3$ | ▷ | H | S | $C_2H_5$ | $OC_2H_5$ | 1.5191 |

TABLE 1-continued

| A | D | E | X | R | R¹ | RI (25°) M.p. °C. |
|---|---|---|---|---|----|-------------------|
| —CH₃ |  | H | O | C₂H₅ | OC₂H₅ | |
| —CH₃ |  | H | S | C₂H₅ | NHCH(CH₃)₂ | 83.5–84 |
| —CH₃ |  | H | S | C₂H₅ | SCH₂CH₂CH₃ | 1.5509 |
| —CH₃ |  | H | S | C₂H₅ | C₆H₅ | 1.5746 |
| —CH₃ | 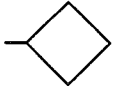 CH₃ | CH₃ | S | CH₂CH₂CH₂CH₃ | SCH₂CH(CH₃)₂ | |
| —CH₃ |  | H | O | C₂H₅ | NHCH(CH₃)₂ | |
| —CH(CH₃)₂ |  | CH₃ | S | C₂H₅ | SCH₂CH(CH₃)₂ | |
| —C(CH₃)₃ |  | Cl | S | CH₃ | OCH₃ | |
| —C(CH₃)₃ |  | H | S | CH₃ | CH₃ | |
| —C(CH₃)₃ |  | H | S | C₂H₅ | OC₂H₅ | 1.5044 |
| —C(CH₃)₃ |  | H | S | C₂H₅ | NHC₂H₅ | 1.5164 |
| —CH₂CH(CH₃)₂ | 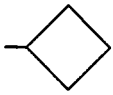 | H | S | CH₂CH₂CH₂CH₃ | NHCH₂CH(CH₃)₂ | |
| —CH₂CH₂CH₂CH₃ |  | H | S | C₂H₅ | NHCH(CH₃)C₂H₅ | |
|  |  | H | S | C₂H₅ | OC₂H₅ | 1.5314 |
|  |  | C₂H₅ | O | CH₂CH₂CH₃ | OCH₂CH₂CH₃ | |
|  CH₃ |  | H | S | C₂H₅ | OC₂H₅ | |

TABLE 1-continued

Structure: pyrimidine ring with substituents A, D, E and O-P(=X)(R¹)(OR) group

| A | D | E | X | R | R¹ | RI (25°) M.p. °C. |
|---|---|---|---|---|---|---|
| cyclobutyl | cyclopropyl | H | O | $C_2H_5$ | $OC_2H_5$ | |
| cyclobutyl | cyclobutyl | H | S | $CH_3$ | $NHCH_2CH_2CH_2CH_3$ | |
| —$SCH_3$ | cyclopropyl | H | S | $C_2H_5$ | $OC_2H_5$ | 1.5522 |
| —$SCH_3$ | cyclopropyl | $CH_2CH_2CH_2CH_3$ | S | $C_2H_5$ | $SCH_2CH_2CH_3$ | |
| —$SCH(CH_3)_2$ | cyclopropyl | H | S | $C_2H_5$ | $OC_2H_5$ | 1.5402 |
| —$SCH(CH_3)_2$ | cyclopropyl | H | S | $C_2H_5$ | $NHC_2H_5$ | 1.5534 |
| —$SCH_2CH_2CH_2CH_3$ | cyclopropyl | H | O | $C_2H_5$ | $SCH_2CH_2CH_3$ | |
| —$SCH_2CH_2CH_2CH_3$ | cyclobutyl | $CH_3$ | O | $CH(CH_3)_2$ | $SCH_2CH(CH_3)_2$ | |
| —$S(O)C_2H_5$ | cyclopropyl | $C_2H_5$ | S | $CH_2CH(CH_3)_2$ | $NHCH_3$ | |
| —$SO_2CH_3$ | cyclopropyl | H | S | $C_2H_5$ | $OC_2H_5$ | 1.5509 |
| —$N(CH_3)_2$ | cyclopropyl | H | S | $C_2H_5$ | $OC_2H_5$ | 1.5344 |
| —$N(CH_3)_2$ | cyclopropyl | H | S | $C_2H_5$ | $NHC_2H_5$ | 1.5484 |
| —$N(C_4H_9)_2$ | cyclopropyl ($CH_3$ substituted) | H | S | $C_2H_5$ | $NHCH_2CH_2CH_3$ | |
| —$N(C_2H_5)_2$ | cyclobutyl | H | S | $C_2H_5$ | $OC_2H_5$ | |

TABLE 1-continued $$\begin{array}{c} D \\ N \\ A \end{array} \begin{array}{c} \\ \\ N \end{array} \begin{array}{c} E \\ \\ O-P \end{array} \begin{array}{c} X \\ \| \\ OR \end{array} R^1$$

| A | D | E | X | R | R¹ | RI (25°) M.p. °C. |
|---|---|---|---|---|---|---|
| —N(C₃H₇)₂ | cyclobutyl | H | O | CH₃ | C₂H₅ | |
| —C₆H₅ | cyclopropyl | H | S | C₂H₅ | OC₂H₅ | 1.5705 |
| —C₆H₅ | cyclopropyl | H | S | C₂H₅ | SCH₂CH₂CH₃ | |
| —OCH₃ | cyclopropyl | H | S | C₂H₅ | OC₂H₅ | 1.5220 |
| —OCH₃ | cyclopropyl | H | S | C₂H₅ | NHC₂H₅ | 1.5279 |
| —OCH₃ | cyclopropyl | CH₃ | S | CH₃ | OCH₃ | |
| —OC₂CH₂CH₂CH₃ | 1-methylcyclopropyl | H | S | CH₂CH₂CH₃ | OCH₂CH₂CH₃ | |
| —CF₃ | cyclopropyl | H | S | C₂H₅ | OC₂H₅ | 1.4814 |
| —CF₃ | cyclopropyl | H | S | C₂H₅ | NHC₂H₅ | 1.4967 |
| —CF₃ | cyclopropyl | C₃H₇ | O | CH₂CH₂CH₂CH₃ | SCH₂CH(CH₃)₂ | |
| —C₂F₅ | cyclobutyl | H | S | C₂H₅ | OC₂H₅ | |
| —C₃F₇ | 1-methylcyclopropyl | H | O | C₂H₅ | SCH₂CH(CH₃)₂ | |

The compounds of the present invention are very effective for the kill and control of insects found on the roots or aerial portions of growing plants.

Representative of the various insects which are killed and controlled by the active compounds of the present invention include the mites (Acarina) in particular, the spider mites (Tetranychidae) such as the two-spotted spider mites (*Tetranychus urticae*), carmine spider mite (*Tetranychus cinnabarinus*) and the European red mite (*Panonychus ulmi*), blister mites, for example, the currant blister mite (*Eriophyes ribis*) and tarsonemids, for example, the broad mite (*Hemitarsonemus latus*), the cyclamen mite (*Tarsonemus pallidus*); leafhoppers and planthoppers, i.e., aster leafhopper (*Macrosteles fascifrons*), rice green leafhopper (*Nephotettix virescens*), zig-zag leafhopper (*Recilia dorsalis*), (*Nephotettix apicalis*), white-back planthopper (*Sogattella furcifera*), brown planthopper (*Nilaparvata lugens*), smaller brown planthopper (*Laodelphax striatellus*), grape leafhopper (*Erythroneura sp*) and potato leafhopper (*Empoasca fabae*); for insects such as aphids (Aphididae) such as the green peach aphid (*Myzus persicae*), the bean aphid (*Aphis fabae*), the black cherry aphid (*Myzus ceraci*), the pea aphid (*Acythorsiphum pisum*) and the potato aphid (*Macrosiphum euphorbiae*), the currant gall aphid (*Cryptomyzus ribis*), the mealy apple aphid (*Sappaphis mali*), the mealy plum aphid (*Hyalopterus pruni*), the cotton aphid (*Aphis gossyppii*); and other such insects including tobacco budworms (*Heliothis virescens*), Western spotted cucumber beetle (*Diabrotica undecimpunctata undecipunctata*), housefly (*Musca domestica*), beet armyworm (*Spodoptera exigua*), and codling moth (*Laspeyresica pomonella*). Borers such as the rice stem borer (Chilo sp), the pink borer (Sesamia sp) and the paddy borer (Tryporyza sp).

In the present specification and claims, the term "systemic" defines the translocation of the active compound employed in the present method through the plant. The active compound can be applied either to the above-ground or preferably to below-ground portions of the plant.

The application of an insecticidally effective amount of an active compound of the present invention is critical to the method of the present invention. The active compound can sometimes be employed in unmodified form. Frequently, however, for easier application, the compound is modified by the employment with it of an adjuvant or inert carrier therefor. Therefore, the practical employment of the beneficial utilities of the present compound often requires that the compound be composited with one or more adjuvant substances which are chemically inert to the active compound, and the resulting compositions are comprehended within the present invention.

The compositions can be formulated in various forms, such as emulsifiable concentrates, wettable powders, flowable suspension dusts, granules, microencapsulated granules, fine granules, oil sprays, aerosols, and the adjuvant employed can be any one or a plurality of materials including aromatic solvents, petroleum distillates, water, or other liquid carriers, propellant substances, surface-active dispersing agents, light absorbers, and finely divided carrier solids. In such compositions, the adjuvant cooperates with the active compound so as to obtain a composition to facilitate the method of the present invention, and to obtain an improved result. The use of either a surface-active dispersing agent or a finely divided carrier solid and the use of both a surface-active dispersing agent and a finely divided carrier solid, simultaneously, constitute preferred embodiments of the method of the present invention. Another preferred embodiment of the present invention is a composition comprising one or more of the presently claimed compounds, an organic liquid as a solvent and carrier therefor, and a propellant material. Numerous other embodiments will become available to those skilled in the art in view of the teachings set forth hereinbelow.

The exact concentration of the active compound in a composition thereof with an adjuvant therefor can vary; it is only necessary that the active compounds be present in a sufficient amount so as to make possible the application of an insecticidally effective dosage. Generally, for practical applications, the active compounds can be broadly applied to the plants or to the soil around the roots of the plants or to water, such as in broadcast rice paddy applications in compositions containing from about 0.00001 percent to about 98 percent by weight of the active compound.

In preparation of dust compositions, the product can be compounded with any of the finely divided carrier solids such as prophyllite, diatomaceous earth, gypsum and the like. In such operations, the finely divided carrier is ground or mixed with the active compound, as active agent, or wetted with a solution of the active agent in a volatile organic solvent. Similarly, dust compositions containing the active product can be similarly compounded from various of the solid dispersing agents, such as fuller's earth, attapulgite and other clays. These dust compositions can be employed as treating compositions or can be employed as concentrates and subsequently diluted with additional solid dispersing agent or with pyrophyllite, diatomaceous earth, gypsum and the like to obtain the desired amount of active agent in a treating composition. Also, such dust compositions can be dispersed in water, with or without the aid of surfactant, to form spray mixtures.

Further, the active compound or a dust concentrate composition containing said compound can be incorporated in intimate mixture with surface-active dispersing agents such as ionic and nonionic emulsifying agents to form spray concentrates. Such concentrates are readily dispersible in liquid carriers to form sprays containing the toxicant in any desired amount. The choice of dispersing agent and amount thereof employed are determined by the ability of the agent to facilitate the dispersion of the concentrate in the liquid carrier to produce the desired spray composition.

In the preparation of liquid compositions, the active compound can be compounded with a suitable water-immiscible organic liquid and a surface-active dispersing agent to produce an emulsifiable liquid concentrate which can be further diluted with water and oil to form spray mixtures in the form of oil-in-water emulsions. In such compositions, the carrier comprises an aqueous emulsion, that is, a mixture of water-immiscible solvent, emulsifying agent and water. Preferred dispersing agents to be employed in these compositions are oil-soluble and include the nonionic emulsifiers such as the polyoxyethylene derivatives of sorbitan esters, complex ether alcohols and the like. However, oil-soluble ionic emulsifying agents such as mahogany soaps can also be used. Suitable organic liquids to be employed in the compositions include petroleum oils and distillates, toluene liquid holohydrocarbons and synthetic organic oils. The surface-active dispersing agents are usually employed in liquid compositions in the amount of from 0.1 to 20 percent by weight of the combined weight of the dispersing agent and active compound.

When operating in accordance with the present invention, the active compound or a composition containing the active compound is applied to the plants or to their habitat in any convenient manner, for example, by means of hand dusters or sprayers. Application to the foliage of the rice plants is conveniently carried out with power dusters, boom sprayers and fog sprayers. In such foliar applications, the employed compositions should not contain any appreciable amounts of any phytotoxic diluents. In large scale operations, dusts, or low-volume sprays can be applied from an airplane.

In further embodiments, one of the compounds of the present invention or compositions containing the same, can be advantageously employed in combination with one or more additional pesticidal compounds. Such additional pesticidal compounds may be insecticides, nematocides, arthropodicides, herbicides, fungicides or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use, or as an additament. The compounds in combination can generally be present in the ratio of from about 1 to about 99 parts of the compound of the present invention with from about 99 to about 1 part of the additional compound(s).

Dosage amounts are generally from 15–1,000 grams (g) preferably from 40–600 g of active compound and most preferably from 125–500 g of active compound per hectare. However, in special cases, it is possible to exceed or reduce the amount and this may sometimes be necessary.

EXAMPLE II

Aqueous dispersions were prepared by admixing O,O-diethyl O-(6-cyclopropyl-2-methyl-4-pyrimidinyl)phosphorothioate with a predetermined quantity of water and a predetermined amount of a surfactant to give aqueous dispersions containing varying predetermined amounts of the compound as the sole toxicant.

Separate rice plants were dipped into one of the dispersions and permitted to dry.

A plastic cylinder was placed around each of the plants and 10 adult aster leafhoppers were placed in the cylinder and the cylinder capped. In a like manner, 10 adult aster leafhoppers were placed on control plants which had been dipped in a solution containing only water and surfactant. The plants were maintained under conditions conducive to the growth of the plants and leafhoppers. After a period of three days, the cylinder and plants were examined to determine the concentration in parts of the active compound per million parts of the ultimate dispersion necessary to give 100 percent kill and control of the aster leafhopper. It was found that at a dosage rate of 1.5 parts of the active compound per million parts of the ultimate dispersion (ppm) the compound gave 100 percent kill and control of aster leafhoppers.

EXAMPLE III

Aqueous dispersions were prepared by admixing one of the hereinafter set forth compounds with a predetermined quantity of water and a predetermined amount of a surfactant to give aqueous dispersions containing varying predetermined amounts of one of the compounds as the sole toxicant.

Separate rice plants were treated by adding a predetermined amount of one of the test dispersions to the root of the plant to determine systemic activity.

A plastic cylinder was placed around each of the plants and 10 adult aster leafhoppers were placed in the cylinder and the cylinder capped. In a like manner, 10 adult aster leafhoppers were placed on control plants which were treated at the root zone with a solution containing only water and surfactant. The plants were maintained under conditions conducive to the growth of the plants and leafhoppers. After a period of three days, the cylinder and plants were examined to determine the concentration in parts of the active compound per million parts of the ultimate dispersion necessary to give 100 percent kill and control of the aster leafhopper. It was found that at a dosage rate of 25 parts of the active compound per million parts of the ultimate dispersion (ppm) each of the compounds O,O-diethyl O-(6-cyclopropyl-4-pyrimidinyl) phosphorothioate, O,O-diethyl O-(6-cyclopropyl-2-methyl-4-pyrimidinyl) phosphorothioate and N-ethyl O-ethyl O-(6-cyclopropyl-4-pyrimidinyl) phosphoramidothioate gave 100 percent kill and control of the aster leafhopper.

Preparation of Starting Materials

The 6-cycloalkyl-4-pyrimidinols employed as intermediates in the preparation of the present compounds are for the most part known compounds, and all can be prepared according to methods described in the literature.

For example 6-cyclopropyl-2-methyl-4-pyrimidinol, 6-cyclopropyl-2-methylthio-4-pyrimidinol, 6-cyclopropyl-2-methoxy-4-pyrimidinol and 6-cyclopropyl-2-methoxy-5-methyl-4-pyrimidinol can be prepared according to the method of M. Zimmermann, U.S. Pat. No. 3,457,278 (1969) in which acetamidine hydrochloride, S-methylisothiourea sulfate or O-methylisourea hydrochloride, respectively, is reacted with β-oxocyclopropanepropionate or with α-methyl-β-oxocyclopropanepropionate.

6-Cyclopropyl-4-pyrimidinol can be prepared by desulferization of 6-cyclopropyl-2-mercapto-4-pyrimidinol with Raney nickel (M. Zimmermann, U.S. Pat. No. 3,457,278).

5-Chloro-6-cyclopropyl-4-pyrimidinol is obtained from 6-cyclopropyl-4-pyrimidinol and N-chlorosuccimimide (M. Zimmermann, U.S. Pat. No. 3,457,278).

What is claimed is:

1. A compound corresponding to the formula

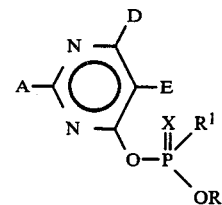

wherein
A represents hydrogen, alkyl, cycloalkyl, alkoxy, perfluoroloweralkyl, alkylthio, alkylsulfinyl, alkylsulfonyl, dialkylamino or phenyl;
D represents cyclopropyl, 1-methylcyclopropyl or cyclobutyl;
E represents hydrogen alkyl or halo;
X represents oxygen or sulfur;
R represents alkyl; and
$R^1$ represents alkyl, alkoxy, alkylthio, monoalkylamino or phenyl.

2. A compound as defined in claim 1 wherein D is cyclopropyl.

3. A compound as defined in claim 2 wherein A is hydrogen.

4. The compound as defined in claim 3 which is O,O-diethyl O-(6-cyclopropyl-4-pyrimidinyl)phosphorothioate.

5. The compound as defined in claim 3 which is N-ethyl O-ethyl O-(6-cyclopropyl-4-pyrimidinyl)phosphoramidothioate.

6. A compound as defined in claim 2 wherein A is alkyl.

7. The compound as defined in claim 6 which is O,O-dimethyl O-(6-cyclopropyl-2-methyl-4-pyrimidinyl)-phosphorothioate.

8. The compound as defined in claim 6 which is O,O-diethyl O-(6-cyclopropyl-2-methyl-4-pyrimidinyl)phosphorothioate.

9. The compound as defined in claim 1 wherein A is perfluoroloweralkyl.

10. The compound as defined in claim 9 which is O,O-diethyl O-(6-cyclopropyl-2-(trifluoromethyl)-4-pyrimidinyl) phosphorothioate.

11. An insecticidal composition comprising an inert carrier in intimate admixture with an insecticidally effective amount of an active compound corresponding to the formula

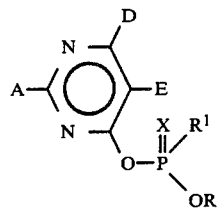

wherein
  A represents hydrogen, alkyl, cycloalkyl, alkoxy, perfluoroloweralkyl, alkylthio, alkylsulfinyl, alkylsulfonyl, dialkylamino or phenyl;
  D represents cyclopropyl, 1-methylcyclopropyl or cyclobutyl;
  E represents hydrogen, alkyl or halo;
  X represents oxygen or sulfur;
  R represents alkyl; and
  $R^1$ represents alkyl, alkoxy, alkylthio, monoalkylamino or phenyl.

12. A composition as defined in claim 11 wherein D is cyclopropyl.

13. A composition as defined in claim 12 wherein A is hydrogen.

14. The composition as defined in claim 13 wherein the active compound is O,O-diethyl O-(6-cyclopropyl-4-pyrimidinyl) phosphorothioate.

15. The composition as defined in claim 13 wherein the active compound is N-ethyl O-ethyl O-(6-cyclopropyl-4-pyrimidinyl) phosphoramidothioate.

16. A composition as defined in claim 6 wherein A is alkyl.

17. The composition as defined in claim 16 wherein the active compound is O,O-dimethyl O-(6-cyclopropyl-2-methyl-4-pyrimidinyl) phosphorothioate.

18. The composition as defined in claim 16 wherein the active compound is O,O-diethyl O-(6-cyclopropyl-2-methyl-4-pyrimidinyl) phosphorothioate.

19. The composition as defined in claim 11 wherein A is perfluoroloweralkyl.

20. The composition as defined in claim 19 wherein the active compound is O,O-diethyl O-(6-cyclopropyl-2-(trifluoromethyl)-4-pyrimidinyl) phosphorothioate.

21. A method for the kill and control of insects which comprises contacting said insects or their habitat with a composition comprising an inert carrier in intimate admixture with an insecticidally effective amount of an active compound corresponding to the formula;

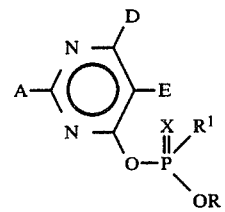

wherein
  A represents hydrogen, alkyl, cycloalkyl, alkoxy, perfluoroloweralkyl, alkylthio, alkylsulfinyl, alkylsulfonyl, dialkylamino or phenyl;
  D represents cyclopropyl, 1-methylcyclopropyl or cyclobutyl;
  E represents hydrogen, alkyl or halo;
  X represents oxygen or sulfur;
  R represents alkyl; and
  $R^1$ represents alkyl, alkoxy, alkylthio, monoalkylamino or phenyl.

22. A method as defined in claim 21 wherein D is cyclopropyl.

23. A method as defined in claim 22 wherein A is hydrogen.

24. The method as defined in claim 23 wherein the active compound is O,O-diethyl O-(6-cyclopropyl-4-pyrimidinyl) phosphorothioate.

25. The method as defined in claim 23 wherein the active compound is N-ethyl O-ethyl O-(6-cyclopropyl-4-pyrimidinyl) phosphoramidothioate.

26. A method as defined in claim 11 wherein A is alkyl.

27. The method as defined in claim 26 wherein the active compound is O,O-dimethyl O-(6-cyclopropyl-2-methyl-4-pyrimidinyl) phosphorothioate.

28. The method as defined in claim 22 wherein the active compound is O,O-diethyl O-(6-cyclopropyl-2-methyl-4-pyrimidinyl) phosphorothioate.

29. The method as defined in claim 21 wherein A is perfluoroloweralkyl.

30. The method as defined in claim 29 wherein the active compound is O,O-diethyl O-(6-cyclopropyl-2-(trifluoromethyl)-4-pyrimidinyl) phosphorothioate.

* * * * *